United States Patent [19]

Lemonnier

[11] 4,397,945
[45] Aug. 9, 1983

[54] TEST METHOD AND APPARATUS FOR THE PRESENCE OF MICROORGANISM IN SYRINGE

[75] Inventor: Jean Lemonnier, Le Vesinet, France

[73] Assignee: Millipore Corporation, Bedford, Mass.

[21] Appl. No.: 272,226

[22] Filed: Jun. 10, 1981

[51] Int. Cl.³ .................. C12Q 1/22; C12M 1/00; C12M 1/26
[52] U.S. Cl. .................. 435/31; 435/287; 435/292
[58] Field of Search .................. 435/29, 30, 31, 34, 435/287, 292

[56] References Cited
U.S. PATENT DOCUMENTS 4,036,698  7/1977  Bush et al. .................. 435/31
4,292,405  9/1981  Mascoli et al. .................. 435/31

Primary Examiner—Robert J. Warden
Attorney, Agent, or Firm—Paul J. Cook; David Prashker

[57] ABSTRACT

A method and apparatus for testing the sterility of the contents of a syringe and the sterility of the internal and external surfaces of a needle connected to the syringe or the contents of a syringe and the sterility of the tip of the syringe nipple (in those cases where the syringe is not fitted with a needle). The needle is inserted into a tube by penetrating a small hole in an adaptor connected to one end of the tube. The adaptor includes a recess so that the syringe and needle can be stably positioned relative to the tube. The tube includes a liquid outlet adjacent to the adaptor so that the liquid contents of the syringe exiting from the needle washes the outside surface of the needle or the tip of the syringe needle before leaving the tube. The liquid leaving the tube is cultured and incubated to determine whether microorganisms are present therein.

8 Claims, 3 Drawing Figures

TEST METHOD AND APPARATUS FOR THE PRESENCE OF MICROORGANISM IN SYRINGE

BACKGROUND OF THE INVENTION

This invention relates to a method and apparatus for testing for the presence of microorganisms.

At the present time, it is necessary to perform sterility tests on samples of pharmacological compositions and apparatus to comply with federal regulations in the United States and similar regulations in other nations.

Any such testing procedure must prevent adventitious microbial growth transmitted to the article or composition being tested or to the substrate containing a test culture medium from the environment; otherwise the test results are invalid. Therefore, it is necessary to demonstrate that the proper precautions have been taken to exclude extraneous microorganisms throughout the test period.

When testing sterilized articles of such a size and shape as to permit complete immersion in 1000 ml of culture medium, the exterior of the device is cleansed with a suitable decontaminating agent and the access to the contents of the device must be made in a suitable aseptic manner. In the special instance of testing devices having a hollow tube, such as transfusion or infusion assemblies, e.g., a syringe having a needle, it is necessary to demonstrate that the contents of the syringe are sterile and that the outside surface of the needle which enters the patient also is sterile. In the prior art procedure, it is common practice to inject the contents of the syringe into a growth medium, remove the needle and immerse the needle also in a growth medium. Typically, for bacteria, a thioglycollate medium has been utilized which includes a resayurin additive to provide for color indication, and also agar to inhibit diffusion throughout the medium. A medium which is particularly useful for determining the presence of fungi is soybean-casein digest medium. Another medium which is utilized for this latter purpose is sabourin. The presently utilized technique for testing sterilized needles requires two weeks incubation time and increases the risk of hand contamination of the needle, thereby causing an excessive number of false positive tests. Obviously, false positive tests are undesirable, for example, since they require resterilization of the entire batch or product which increases the risk of ruining the batch or product. Also, this direct method is somewhat limited since it requires a specific volumetric to area ratio, in order to control the oxygenation of the medium, and these volumetric ratios are sometimes difficult to achieve in practice.

It would be highly desirable to provide a procedure for testing the contents of a syringe which also permits testing the inside and outside surface of a needle that may be associated with the syringe for microorganisms or which also permits testing the tip of the syringe nipple (for syringes without a needle) for microorganisms in a single step procedure. It would also be desirable to provide such a test which eliminates or minimizes the risk of hand contamination during the test procedure. Furthermore, it would be desirable to provide such a test which eliminates the requirement for accurately maintaining specific volumetric to area ratios within the medium.

SUMMARY OF THE INVENTION

In accordance with this invention, the contents of a syringe which may have a needle associated therewith, are tested for sterility using a special adaptor. The adaptor is covered by a cap. After the cap has been removed, the syringe and needle are retained in a desired stable position during testing. The needle, after insertion, is located within the central portion of a tube at a distance less than 3 mm, preferably between about 0.5 mm and about 2 mm from the inner surfaces of the tube. By so-positioning the needle, any liquid which passes between the outer surface of the needle and the inner surface of the tube can wash the needle surface under relatively turbulent conditions and in the absence of cavitation so as to assure complete washing of the outer surface of the needle. In addition, the space is sufficiently large as to permit the liquid to pass between the inner surface of the tube and the outer surface of the needle. The needle and syringe is tightly seated within a cavity on the outside surface of the adaptor in order to retain the desired positioning of the needle within the tube. One end of the tube is in fluid communication with a means for filtering the liquid under sterile conditions in order to test the liquid for microorganisms. The exit port from the tube must be located adjacent to the tube end through which the needle is inserted so that the liquid washes the entire needle surface prior to exiting from the tube. The other end of the tube can be either closed or rendered in fluid communication with a sterile liquid when it is desired to sterilize the inside of the tube, thereby to permit repeated use of the tube for testing.

In operation, a needle connected to a syringe is inserted through the adaptor into the tube so that it is stabilized within the tube at a position less than about 3 mm from the inside surface of the tube. The contents of the syringe then are passed through the needle into the tube, around the outside surface of the needle and then to a means for filtering the liquid under sterile conditions so that any microorganisms can be isolated on the filter and can be exposed to a culture medium suitable for growth of a particular class of microorganisms. Insertion of the needle into the tube and emptying of the syringe is repeated, usually about 20 times, to produce a representative sample. After the last syringe has been emptied, a sterilizing liquid may be passed through the tube into the means for filtering the liquid. Thereafter, a culture medium is injected into the container means for the filter in order to promote growth of microorganisms on the filter.

Any apparatus adapted to permit the practice of sterility testing in accordance with legal regulations can be attached to one end of the tube in accordance with this invention. For example, the apparatus disclosed in U.S. Pat. No. 4,036,698 to Bush et Lemonnier is particularly useful in combination with the present invention. U.S. Pat. No. 4,036,698 is incorporated herein by reference. The apparatus disclosed therein generally comprises a pair of canisters each having two ports at one end and a single port at the opposite end each capable of being hermetically sealed. One of the two ports at one end is provided with a filter capable of allowing air flow in either direction while screening out microorganisms. A second membrane filter is positioned within the cylinder generally parallel to the end having the two ports and spaced apart from that end. The filters sealed at the side walls of the cylinder so that the test product flows through an unfiltered port into the container passes through the second membrane and then out the single port at the opposite end. Microorganism contamination within the test product is trapped on the second membrane filter.

In use, two canisters are connected to the exit opening of the tube by tube means having a Y-shaped splitter so that approximately equal portions of the liquid output from the tube passes into each canister. The liquid passes into the unfiltered port on the two port end of the canister, through the filter in the canister and out the single port at the opposite end of the canister. The size of the openings in the filter is such as to entrap microorganisms while permitting filtered liquid to pass therethrough. After the number of desired samples has been passed from the needle, through the tubes and into the canisters, the sterile solution is introduced into the tube at an end opposite to that wherein the needle is positioned to remove any residues of product material within the tube and within the tubing connecting the tube containing the needle and the canisters. After the samples have been passed into the canisters and have been suitably rinsed, a culture medium suitable for growth of bacteria is flowed into one canister through the unfiltered port at one end while the single port is capped at the opposite end. The last needle and syringe are retained in position in the adaptor and tube while the sterilizing liquid and culture medium(s) are introduced into the tube. During introduction of the culture medium(s), the filtered port on the canister is open to the air to vent air out of the canister while preventing microorganisms within the canister from being removed therefrom. In the case of bacteria testing with a thioglycollate growth medium, the cap over the filter port is replaced after a sufficient period to allow approximately the upper third of the liquid in the canister to be oxidized, a condition indicated by its turning color such as pink. Thereafter, replacement of the cap seals the canister against further aeration and consequently inhibits any further oxidation of the liquid.

In the final step, the single port at one end of the second canister is capped and the filtered port is uncapped to allow venting while a second culture medium such as soybeancasein digest medium, suitable for promoting fungi growth is flowed into the second canister while preventing flow thereof into the first canister. Thereafter, the canisters are capped at all three ports to allow incubation for an appropriate period of time at an appropriate temperature. Visual observation of the color or turbidity of the liquid medium then provides for determination of the presence or absence of contaminant microorganisms in the test product.

DESCRIPTION OF SPECIFIC EMBODIMENTS

Figure 1:
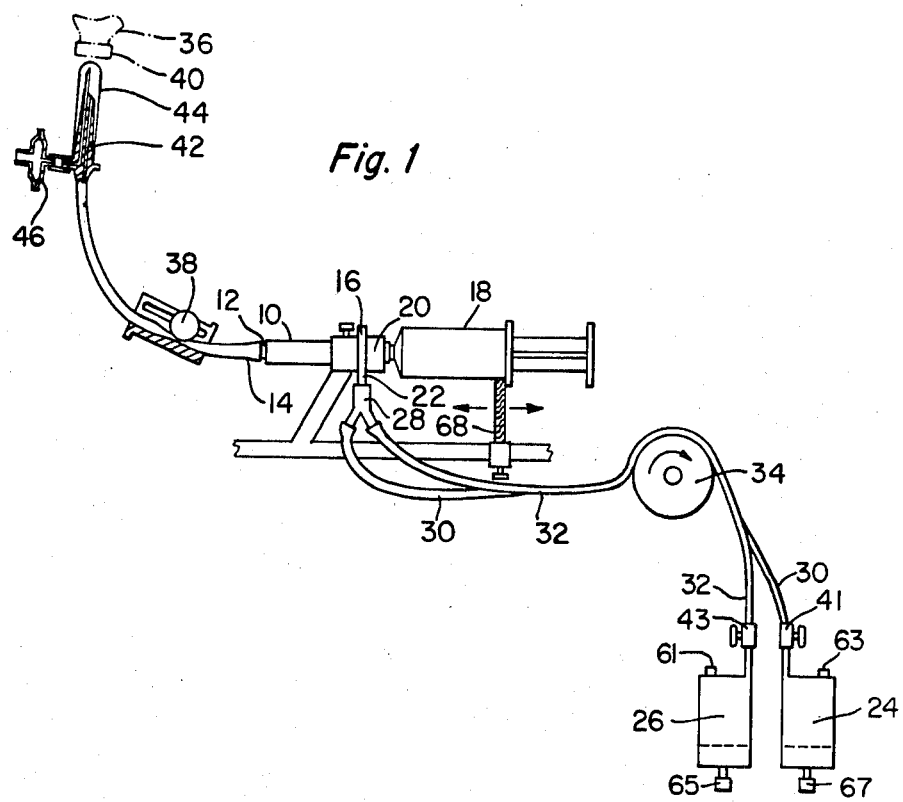
FIG. 1 is a side view showing the apparatus of this invention in use.

Referring to FIG. 1, the apparatus of this invention includes a tube 10 having an internal diameter of a size such that, when a needle is inserted therein axially, the distance between the outside surface of the needle and the inside surface of the tube 10 is less than about 3 mm, preferably between about 2 and about 0.5 mm. A first end 12 of tube 10 is adapted to accommodate a feed tube 14 through which can be fed a sterilizing liquid or a nutrient liquid composition. A second end 16 of tube 10 is adapted to accommodate and position a syringe 18 either alone or in combination with a needle so that the syringe 18 can be stabilized in position while delivering liquid therefrom and into the interior of tube 10. The syringe 18, with or without a needle, fits into adaptor 20 which is formed of a relatively flexible material in order to stabilize the syringe 18 in the desired position and to seal the interior of tube 10 from the atmosphere when syringe 18 is in position. The penetration of the syringe nipple into the adaptor can be limited by an adjustable support 68. A spout 22 also provided at the end 16 of tube 10 in order to remove liquid which is passed within tube 10 to be directed to canisters 24 and 26. The Y-shaped stream splitter 28 fits over spout 22 and is connected to conduits 30 and 32 which, in turn, communicate respectively with canisters 24 and 26. Liquid is pumped through tubes 30 and 32 by means of peristaltic pump 34 or by any other suitable pumping means.

Tube 14 can be closed or opened to communication with container 36 by means of clamp 38, which container can contain a sterilizing liquid or a nutrient growth composition. Container 36 includes a seal 40 which can be penetrated by needle 42 when cap 44 is removed. Filter 46 is provided in order to filter gas passing to the interior of container 36 when liquid is pumped out of it by peristaltic pump 34 therefrom through a second opening within a needle 42 into tube 14 and tube 10.

Figure 2:
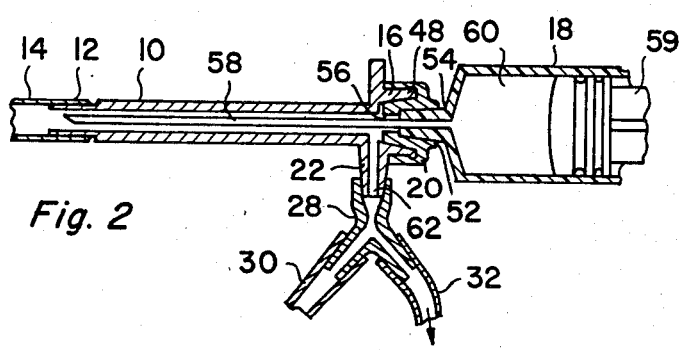
FIG. 2 is a cross sectional view of the apparatus of this invention utilized to test a needle and the contents of the syringes.

Referring to FIG. 2, one end 16 of tube 10 is provided with a shoulder 48 over which is fit to an adaptor 20 which is formed from a relatively flexible plastic or rubber material or the like. The adaptor 20 includes a recess 52 shaped to accommodate the nipple 54 of a standard syringe sufficiently tightly so that the atmosphere is excluded from the interior of tube 10 during testing. The adaptor 20 also includes a small hole 56 located at the bottom of recess 52, which has a minimum diameter to let the needle 58 pass through it without risk of wiping the needle when it is inserted into tube 10. The penetrating of the nipple 54 is limited by the adjustable support 68 to create a small cavity 69 for the rinsing of the tip syringe nipples.

Figure 3:
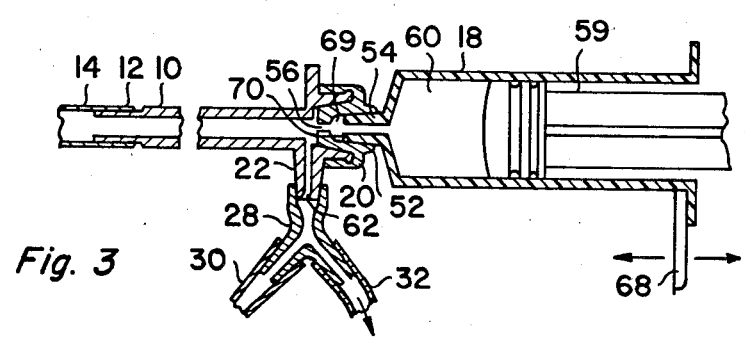
FIG. 3 shows the apparatus of this invention utilized to test the contents of a syringe and the tips of the syringe nipples.

Referring to FIG. 3, the nipple 54 of syringe 18 is inserted into recess 52. When clamp 38 (FIG. 1) is closed, the liquid passes through the cavity 69, through opening 70, into tube 10, conduit 62, Y-shaped splitter 28 and then into tubes 30 and 32.

The operation of this invention will be described with reference to FIGS. 1 and 2. In the first step, a needle 58 associated with syringe 18 is inserted into the small hole 56 such that the nipple 54 seats within cavity 52 in a stable position such that the needle 58 is spaced apart from the inner walls as described above. While clamp 38 is closed, plunger 59 is depressed in order to inject liquid 60 through needle 58 into tube 10 so that the liquid progresses down to clamp 38 and then backwashes the outer surface of the needle 58 along its entire length and then passes out of tube 10 through conduit 62. This liquid is split into aliquots at Y-shaped stream splitter 28 with one aliquot passing through tube 32 into canister 26 and the other aliquot passing through tube 30 into canister 24. The filtered ports 61 and 63 of the two canisters are covered with sealing caps during this step. Each of the aliquots passes through filters positioned within canisters 24 and 26 and then are emptied through aspirating ports 65 and 67. It is convenient to effect filtration of the liquid through the filter and out of the tubes 65 and 67 by means of a vacuum pump or the like (not shown) connected with aspirating tubes 65 and 67. Since a vacuum is utilized, the ports 61 and 63 must be closed to the atmosphere in order to allow the liquid to pass through the canisters 24 and 26. Alternatively, a peristaltic pump 34 can be utilized to act upon tubes 30 and 32 to effect passage of the liquid aliquots through the canisters 24 and 26. After the syringe 18 is emptied, a plurality of other syringes are sequentially emptied in the same manner as described above until a suitable volume of sample liquid has been passed through the filters positioned within canisters 24 and 26. After the last syringe has been emptied, a sterilizing liquid in container 36 may be passed through tubes 14, 10, 30 and 32 in order to completely removed the sample to be tested so that the entire sample is filtered in the manner described above.

The interior of the apparatus may be washed with a sterilizing liquid from container 36. A new container 36 containing a microorganism growth medium is positioned onto needle 44 while clamp 38 is open and one of the clamps 41 or 43 is open while the other of clamps 41 or 43 is closed. For example, when it is desired to promote fungi growth, a soybean-casein digest medium can be utilized. A description of the preparation of such a medium is described in U.S. Pharmacopeia XVIII at page 852. The fungi growth-promoting liquid in container 36 then passes through tubes 14, 10 and 32 and into canister 26 when clamp 43 is open and clamp 41 is closed. When utilizing a vacuum pump, the growth medium is flowed into canister 26 through tube 32 when the vacuum pump (not shown) is connected to filtered port 61, thereby providing prevention of the air from canister 26 without the possibility of introducing any bacterial contamination through this vent. During introduction of this growth medium, port 65 is closed.

After the introduction of the first growth medium such as Sabouraud medium into canister 26, the clamp 43 is closed and clamp 41 is open and a vacuum pump (not shown) is connected to filtered port 63 of canister 24. A new container 36 containing a second microorganism growth medium such as one particularly suitable for promoting growth of bacteria is placed over needle 44 for delivery to canister 24. Typical bacteria growth medium suitable for this purpose comprises a thioglycollate solution, the formation of which is described in the U.S Pharmacopeia XVIII at page 852. The canister 24 is filled with this medium and, after being filled, the port 63 is left open to vent air into the canister for a sufficient period to allow the upper one third of the thioglycollate medium to become oxidized as indicated by its turning pink. After one third of the liquid has become pink, a sealing cap is placed over the port 63 to prevent further oxidation.

In the final step, both canisters 24 and 26 are incubated for a period of 7 days with the canister 24 being sealed at all entry ports to prevent any further oxidation of the medium. The thioglycollate medium is maintained at a temperature of 30°-35° C., while the soybean-casein digest medium is maintained at a temperature between about 20° and 25° C. When, at the end of this period, no turbidity is observed in the solution, the product material is deemed to be free from the contaminant microorganism.

As in any sterility test system, control is run in which a sterile control liquid is substituted for the test product in the entire procedure including the medium and processed in the same fashion as the actual material to be tested. If at the conclusion of the incubation period, microorganism growth has been observed in either of the canisters, a review of the details of the procedure must be carried out to ascertain the source of the contamination. Upon conclusion of the procedure, the canisters 24 and 26 may be disposed of in any suitable manner since they can be made of relatively inexpensive plastic materials.

The sterility testing of syringes, as described herein follows U.S.P. XX page 881.

I claim:

1. Apparatus for testing the sterility of the contents of a syringe and of a needle attached to said syringe which comprises a tube, an adaptor means attached to a first end of said tube, said adaptor means including a small hole, a spout and a recess, said recess adapted to receive and retain said syringe, means for connecting a second end of said tube to a source of a sterile solution in order to establish fluid communication between said tube and said sterile solution source, means to remove the liquid contents of said syringe from said tube through said spout and to direct said liquid into at least one canister adapted to filter said liquid and to grow microorganisms in said liquid in the absence of microorganisms in the surrounding atmosphere.

2. The apparatus of claim 1 where in a needle attached to said syringe is positioned through said small hole and axially within said tube, the outer surface of said needle being between about 0.5 mm and 2 mm from the inner surface of said tube.

3. The apparatus of claim 1 including means to direct liquid from said tube to a plurality of sterile containers, each of said sterile containers including filter means for filtering microorganisms from said liquid.

4. The process for testing the sterility of liquid contents of a syringe, said syringe having a needle attached thereto which comprises forcing said liquid contents from said syringe, through said needle and into a sterile tube, said tube having an inner surface spaced apart from the outer surface of said needle a distance less than about 3 mm, passing the liquid exiting from said needle along the outer surface of said needle within the tube, removing said liquid from said tube by exit means positioned adjacent the point of entry of said needle in said tube, passing said liquid through a filter under sterile conditions, contacting said filter with a growth medium incubating said growth medium and filtered material under sterile conditions and observing any change in said growth medium in order to determine the presence of a microorganism in said liquid or on said needle.

5. The process of claim 4 wherein said growth medium is a thioglycollate solution.

6. The process of claim 4 wherein said growth medium is soybean-casein digest medium.

7. The process of claim 4 wherein said growth medium is Sabouraud medium.

8. The process of claim 4 wherein said liquid exiting from said tube is formed into aliquots and wherein each aliquot is passed through a separate filter under sterile conditions and each of said filters is contacted with a growth medium and incubated.

* * * * *